US009622997B2

(12) United States Patent
Orr

(10) Patent No.: US 9,622,997 B2
(45) Date of Patent: Apr. 18, 2017

(54) METHODS FOR TREATING INSOMNIA

(71) Applicant: Lynn Health Science Institute, Inc., Oklahoma City, OK (US)

(72) Inventor: William C. Orr, Oklahoma City, OK (US)

(73) Assignee: Lynn Health Science Institute, Inc., Oklahoma City, OK (US)

( * ) Notice: Subject to any disclaimer, the term of this patent is extended or adjusted under 35 U.S.C. 154(b) by 0 days.

(21) Appl. No.: 14/404,347

(22) PCT Filed: Mar. 13, 2013

(86) PCT No.: PCT/US2013/030685
§ 371 (c)(1),
(2) Date: Nov. 26, 2014

(87) PCT Pub. No.: WO2013/180796
PCT Pub. Date: Dec. 5, 2013

(65) Prior Publication Data
US 2015/0148420 A1 May 28, 2015

Related U.S. Application Data

(60) Provisional application No. 61/654,174, filed on Jun. 1, 2012.

(51) Int. Cl.
*A61K 31/197* (2006.01)
(52) U.S. Cl.
CPC .................. *A61K 31/197* (2013.01)
(58) Field of Classification Search
None
See application file for complete search history.

(56) References Cited

U.S. PATENT DOCUMENTS

| | | | |
|---|---|---|---|
| 5,149,713 A | 9/1992 | Bousquet | |
| 7,824,697 B2 | 11/2010 | Trissel et al. | |
| 2003/0031711 A1 | 2/2003 | Fara et al. | |
| 2005/0215521 A1 | 9/2005 | Lalji et al. | |
| 2007/0265343 A1 | 11/2007 | Dharmadhikari et al. | |
| 2008/0033274 A1 | 2/2008 | Postius | |
| 2008/0182904 A1 | 7/2008 | Ameisen | |
| 2008/0206332 A1 | 8/2008 | Kidney et al. | |
| 2009/0208554 A1 | 8/2009 | Hobot et al. | |
| 2010/0029770 A1 | 2/2010 | Roberts et al. | |
| 2010/0029771 A1 | 2/2010 | Ameisen | |
| 2010/0137442 A2 | 6/2010 | Sastry et al. | |
| 2010/0255093 A1* | 10/2010 | Edgren | A61K 9/2027 424/468 |
| 2011/0021469 A1 | 1/2011 | Meythaler et al. | |
| 2011/0091542 A1 | 4/2011 | Navon et al. | |
| 2011/0200671 A1 | 8/2011 | Dharmadhikari et al. | |
| 2011/0230493 A1* | 9/2011 | Long | C07D 491/10 514/252.03 |
| 2011/0269836 A1 | 11/2011 | Foster et al. | |

FOREIGN PATENT DOCUMENTS

CA 2265615 3/1998
WO 2005063297 A2 7/2005

OTHER PUBLICATIONS

Orr, W. et al—2012—Neurogastroenterology & Motility 2012 vol. 24 pp. 553-559.*
Lewis, R., Hawley's Condensed Chemical Dictionary, 15th ed., 2007, at p. 711.*
Gagliardi, Gregg S. et al., Effect of Zolpidem on the Sleep Arousal Response to Nocturnal Esophageal Acid Exposure, Clinical Gastroenterology and Hepatology 2009; 7:948-952.
Dean, Bonnie B. et al., The Relationship Between the Prevalence of Nighttime Gastroesophageal Reflux Disease and Disease Severity, Digestive Diseases and Sciences (2010) 55:952-959, Published online Aug. 20, 2009.
Orr, W.C., "Review article: sleep-related gastro-oesophageal reflux as a distinct clinical entity," Ailmentary Pharmacology & Therapeutics 31, 47-56, 2010 Blackwell Publishing Ltd., Epub accepted article Aug. 18, 2009.
Orr, W.C., et al., "The effect of baclofen on nocturnal gastroesophageal reflux and measures of sleep quality: a randomized, cross-over trial," Neurogastroenterology & Motility (2012) 24, 553-e253, Article first published online Mar. 8, 2012.
Lynn Health Science Institute, Inc., Search Report and Written Opinion, PCT/US2013/030685, May 14, 2013.
Office Action issued Oct. 14, 2015 in related Canadian application No. 2874737, Lynn Health Science Institute, Inc.
Orr, W.C. et al., M1863 The Effect of Baclofen on Sleep Measures and Sleep Related Gastroesophageal Reflux (GER), Gastroenterology, vol. 136, No. 5, May 1, 2009, p. A-434, Elsevier, Philadelphia, PA.
American College of Gastroenterology, Baclofen Decreases Reflux, Improving Sleep Quality for Nighttime Heartburn Sufferers, released Oct. 18, 2010, Internet.
Finnimore, A. J. et at., The Effects of the Gaba Agonist, Baclofen, on Sleep and Breathing, European Respiratory Journal, Munksgaard International Publishers, Copenhagen, DK, vol. 8, No. 2, pp. 230-234, Jan. 1, 1995.
Huang Yu-Shu et al., Narcolepsy: Action of Two Gama-Aminobutyric Acid Type B Agonists, Baclofen and Sodium Oxybate, Pediatric Neurology, Jul. 2009, pp. 9-16.
Cui Ranji et al., The Effect of Baclofen on Alterations in the Sleep Patterns Induced by Different Stressors in Rats, Journal of Pharmacological Sciences, vol. 109, No. 4, Apr. 2009, pp. 518-524.

(Continued)

Primary Examiner — Heidi Reese
(74) Attorney, Agent, or Firm — McAfee & Taft

(57) ABSTRACT

Methods for treating insomnia are disclosed. The methods are directed to administering a pharmaceutically effective amount of baclofen to an individual suffering from insomnia. In addition, due to baclofen's positive effects on reducing nighttime reflux events, the present methods are directed to treating insomnia in patients that also suffer from nighttime reflux or gastroesophageal reflux disease (GERD) by administering a pharmaceutically effective amount of baclofen.

10 Claims, 4 Drawing Sheets

(56) References Cited

OTHER PUBLICATIONS

Fass, R. et al., Arbaclofen Placarbil Improves Sleep Quality in Patients with Proton Pump Inhibitor (PPI)-Responsive Gastroesophageal Reflux Disease (GERD), Sleep, vol. 33, Abstract Supplement, 2010, pp. A291-A292.
Search report issued Oct. 21, 2015 in corresponding European application No. 13797515.7, Lynn Health Science Institute Inc.

* cited by examiner

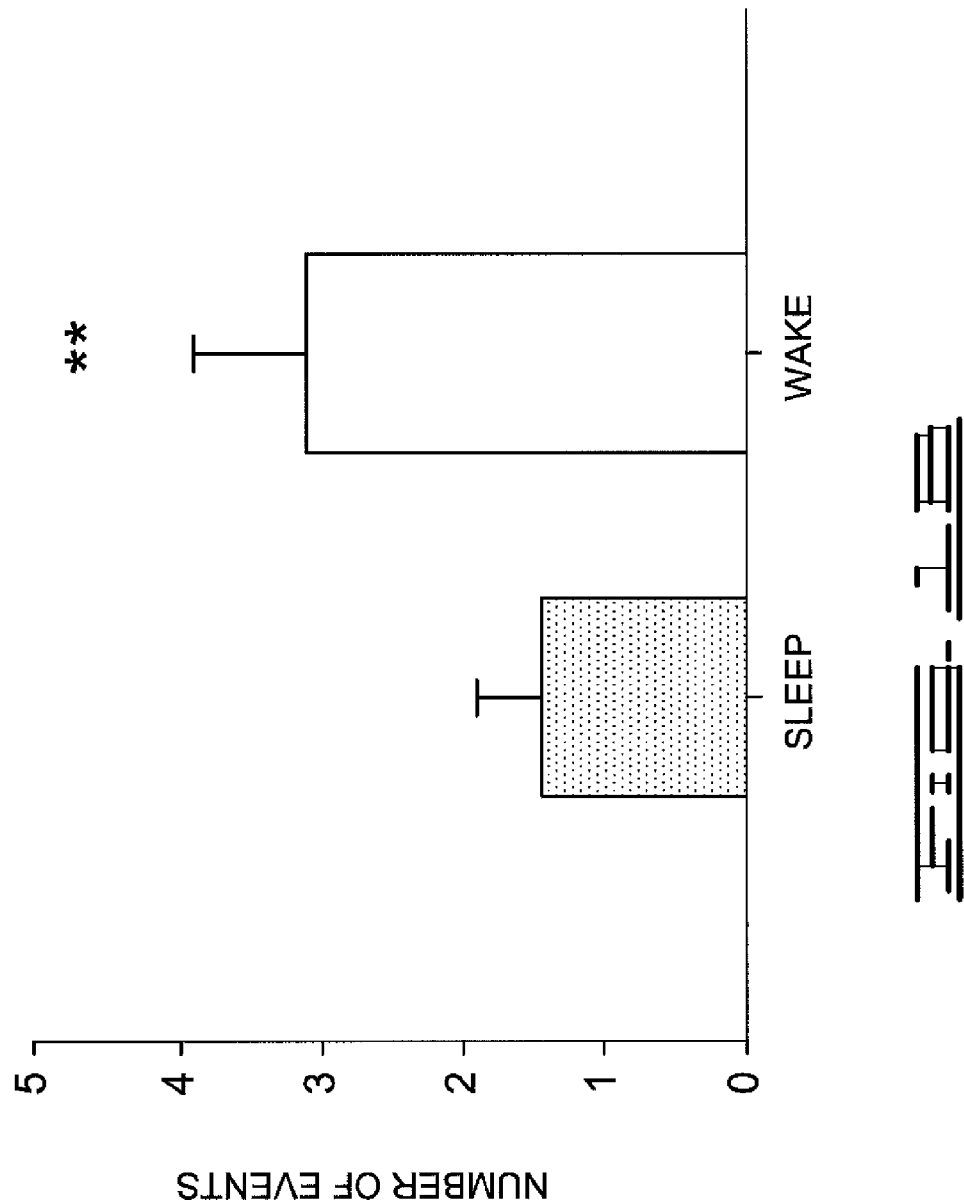

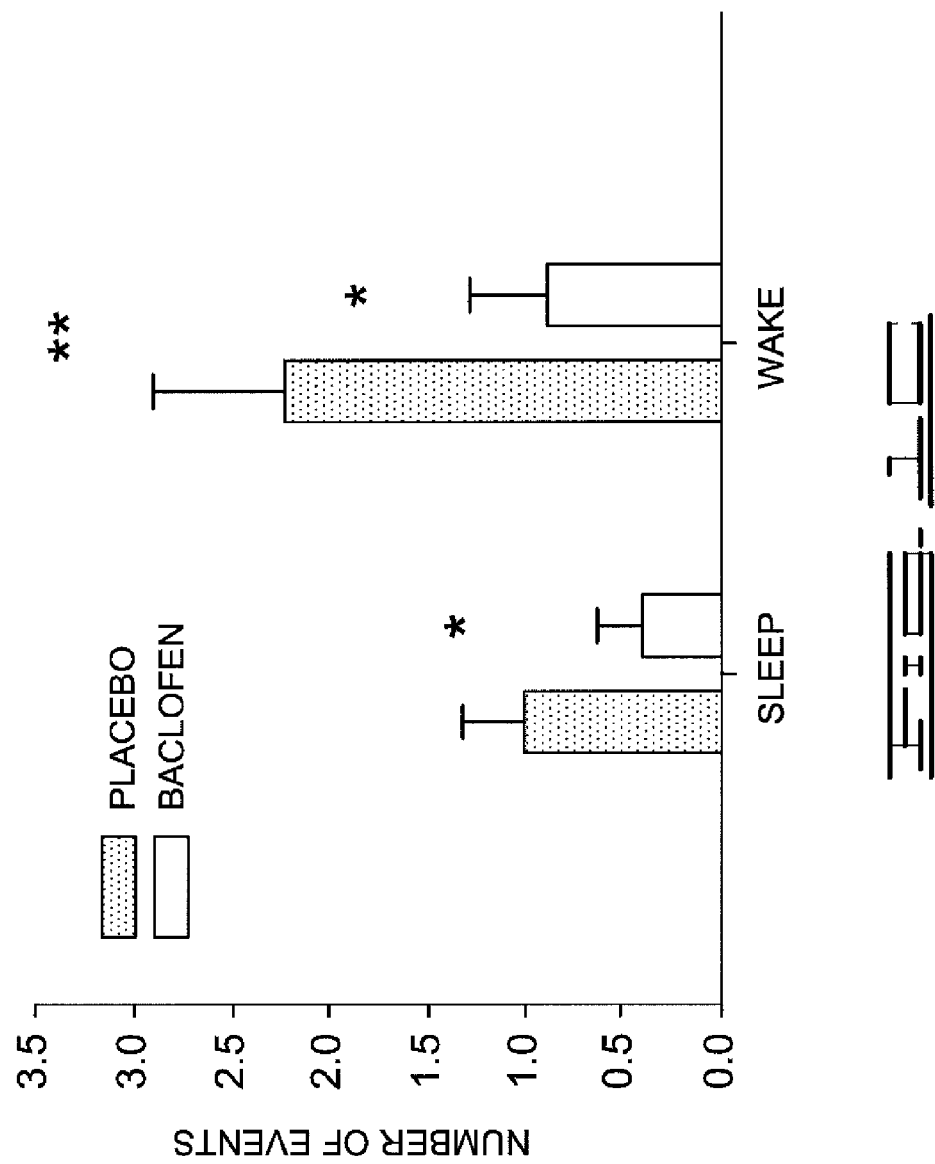

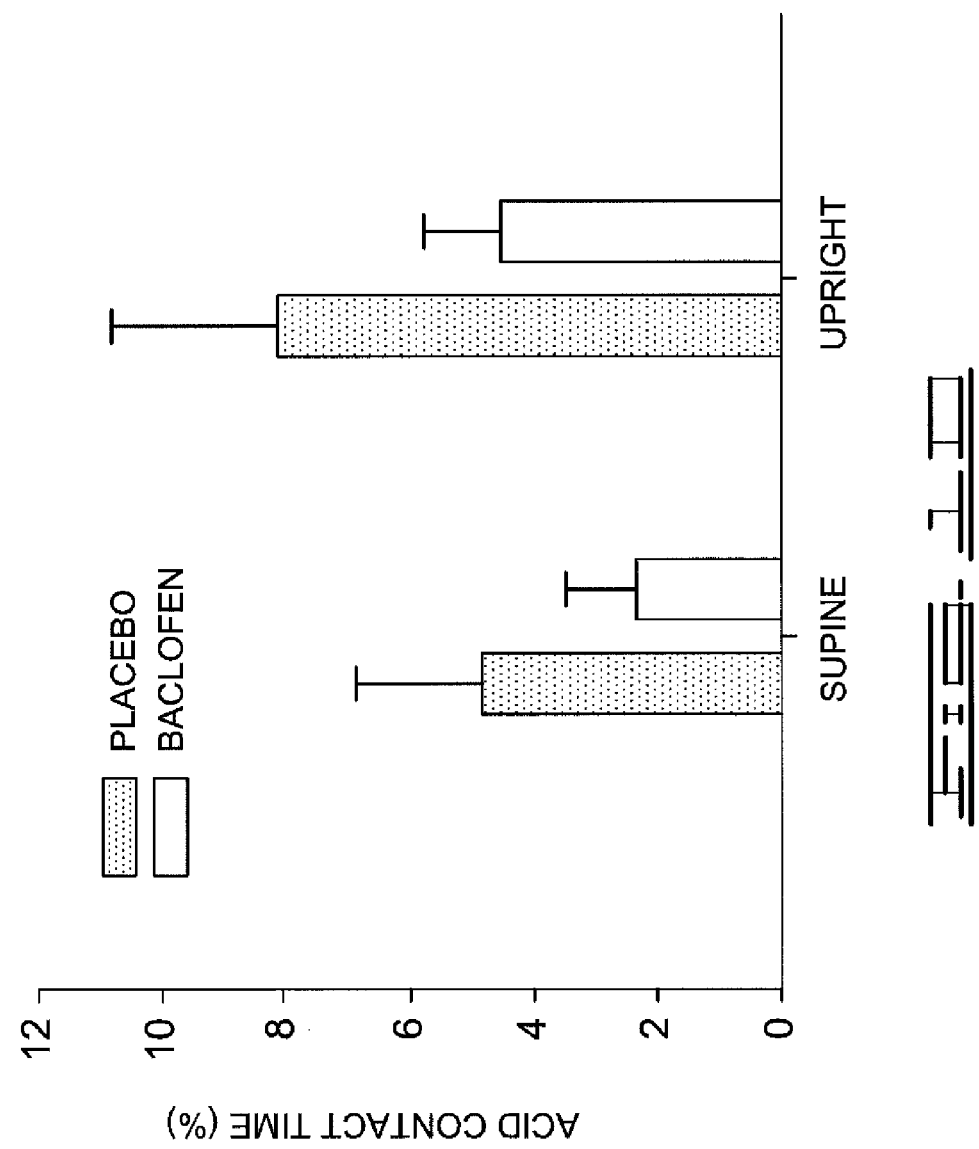

METHODS FOR TREATING INSOMNIA

BACKGROUND

Insomnia and other sleep problems are among the most common complaints dealt with by primary care physicians. Studies have estimated that 33% of the general population and up to 50% of older adults suffer from insomnia and other sleep-related disorders. The common treatments for insomnia are drugs such as zolpidem, temazepam, and doxepin as well as other anti-depressants and anxiolytics. Studies have estimated that these currently available treatments only improve sleep efficiency by <10% and improve total sleep time by less than 10%. Furthermore, the present treatments for insomnia have been associated with numerous deleterious and potentially dangerous side effects such as rebound insomnia upon withdrawal, drowsiness, parasomnias, and amnesia. These treatments typically produce central nervous system (CNS) sedation which prevents a normal arousal response to sleep-related gastroesophageal reflux (GER). This has been shown to result in a prolongation of acid mucosal contact which is a major cause of esophagitis. Thus, these treatments can exacerbate GER in individuals who may suffer from both insomnia and nighttime GER. Accordingly, an improved and safer treatment method for insomnia, particularly insomnia in GERD patients is needed.

Baclofen is a gamma-aminobutyric acid (GABA) receptor agonist that is primarily used to treat spasticity in patients with spinal cord injuries, cerebral palsy, and multiple sclerosis. Studies have demonstrated that baclofen also reduces GER and esophageal acid exposure in healthy individuals and patients with GERD. In addition, baclofen has been investigated as a potential treatment for restless legs syndrome (RLS) and obstructive sleep apnea (OSA). Some of these investigations noted an improvement in sleep parameters associated with improvement in the parameters of interest such as leg movements and obstructive breathing during sleep. The participants in these studies did not suffer from insomnia and the studies did not employ a transient insomnia protocol, therefore baclofen's efficacy as a sleep aid could not be assessed. Thus, to date, baclofen has not been assessed for efficacy in the treatment of individuals with insomnia.

SUMMARY

In one embodiment, a method for treating insomnia comprises administering a pharmaceutically effective amount of baclofen to a patient suffering from insomnia. For example, the pharmaceutically effective amount of baclofen can be from about 1 mg to about 60 mg. In other embodiments, the pharmaceutically effective amount of baclofen can be from about 5 mg to about 55 mg, from about 10 mg to about 50 mg, from about 15 mg to about 45 mg, from about 20 mg to about 40 mg, from about 25 mg to about 35 mg, from 30 mg to about 32.5 mg, and all doses between the above listed ranges. In yet another embodiment, the pharmaceutically effective amount of baclofen can be from about 10 mg to about 40 mg.

The administering step can be administered via oral, sublingual or buccal routes. For example, oral administration of baclofen can be performed through the use of a transmucosal tablet, liquid, capsule, or film. Additionally, baclofen can be administered transdermally, nasally, subcutaneously, or intramuscularly.

The administering step can be performed once daily from about two hours to about thirty minutes prior to the desired sleep time. In one embodiment, the administering step can be performed once daily at about one hour prior to the desired sleep time.

In another embodiment, a method of treatment for insomnia comprises administering a pharmaceutically effective amount of baclofen to a patient suffering from insomnia and an upper gastrointestinal condition such as nighttime GER.

BRIEF DESCRIPTION OF THE DRAWINGS

FIG. 1B is a bar graph representing the total number of reflux events during sleep versus an arousal or awakening after sleep onset for all participants in the study described in Example 2.

FIG. 1C is a bar graph representing the number of reflux events during sleep and arousals after sleep onset (wake) for the placebo and baclofen groups in the study described in Example 2.

FIG. 1D is a bar graph representing the acid contact time (ACT) in the distal esophagus in the upright and recumbent positions (during the sleeping interval) for the placebo and baclofen groups in the study described in Example 2.

DETAILED DESCRIPTION

Figure 1A:
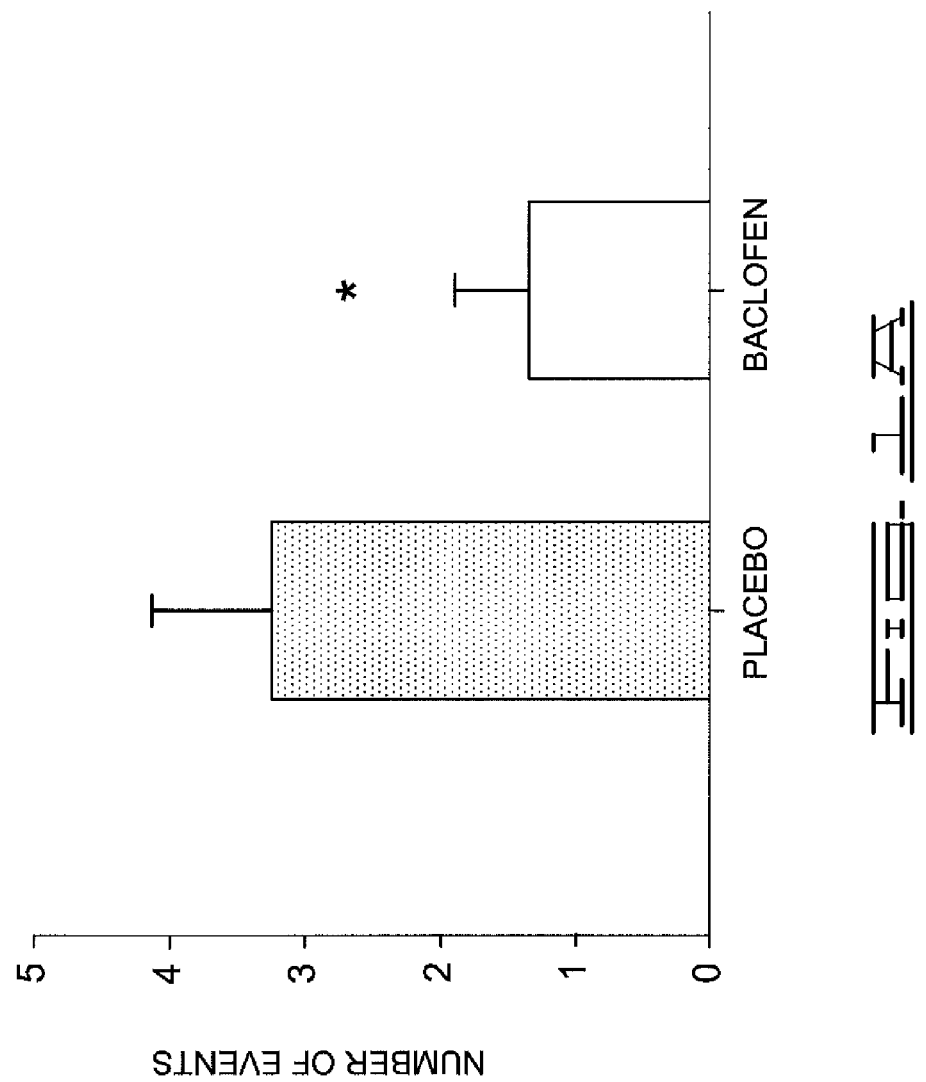
FIG. 1A is a bar graph representing the number of reflux events during the sleeping interval in the distal esophagus for placebo (black bar) and baclofen (white bar) for the study described in Example 2.

The term "pharmaceutically effective amount" as used herein refers to a dose or quantity that causes improvement in at least one objective or subjective sleep parameter deficiency associated with insomnia including, but not limited to: difficulty falling asleep; difficulty maintaining sleep; decrease in total sleep time; persistent waking after sleep onset (WASO); and poor sleep quality. Although the present invention calls for methods of treating insomnia, some primary sleep disorders, such as circadian rhythm disorders, include insomnia as a component of the disorder. Thus, the term "insomnia" should be understood to also include the insomnia component of these disorders.

Insomnia can be described as primary, secondary, or co-morbid. Primary insomnia involves sleep parameter deficiencies not attributable to a medical, environmental, or psychiatric cause. Secondary insomnia includes sleep parameter deficiencies that are associated with another condition. Co-morbid insomnia includes primary insomnia concomitant with one or more other conditions. Insomnia can be further characterized as transient, acute or short-term, and chronic. Transient insomnia refers to sleep parameter deficiencies lasting a few nights. Acute or short-term insomnia refers to sleep parameter deficiencies lasting less than a month. Chronic insomnia refers to sleep parameter deficiencies lasting at least one month.

Unless stated otherwise or specifically designated, the term "baclofen" as used herein refers to 4-amino-3-(4-chlorophenyl)-butanoic acid, its pharmaceutically acceptable salts, and its pharmaceutically acceptable derivatives. Unless stated otherwise or specifically designated, the term "baclofen" also refers to isomers and prodrugs thereof including, but not limited to R-baclofen, S-baclofen, and arbaclofen, and any mixtures thereof.

In one embodiment, a method for treating insomnia with baclofen is provided. The method involves administering a pharmaceutically effective amount of baclofen to an individual suffering from insomnia. In one aspect, the individual is suffering from insomnia. In another aspect, the individual is suffering from chronic insomnia. In yet another aspect, the individual is suffering from acute insomnia. In yet another aspect, the individual is suffering from primary insomnia co-morbid with another condition. In yet another aspect, the individual is suffering from primary insomnia co-morbid with GERD or sleep-related GER.

A method for treating insomnia in patients that also suffer from an upper gastrointestinal condition such as nighttime GER is also provided. The method involves administering a pharmaceutically effective amount of baclofen to an individual suffering from primary insomnia and an upper gastrointestinal condition such as nighttime/sleep-related GER or GERD. Thus, in this instance, the patient continues to experience some degree of insomnia independent of the absence or presence of GER or GERD symptoms. As previously discussed, many of the current treatments for insomnia prevent a normal arousal response to sleep-related GER leading to prolongation of acid mucosal contact which is a major cause of esophagitis and the progression of GERD. However, baclofen has been shown to reduce the number of sleep-related reflux events thereby reducing acid contact time (see Example 2). This, in combination with its effectiveness in improving sleep parameters in a well-established insomnia model (see Example 1), baclofen provides a therapeutic option for treating insomnia in patients that also suffer from sleep-related GER or GERD. Furthermore, it should be noted that a recent study has shown that a widely used hypnotic drug (zolpidem) has a distinctly negative effect on sleep related GER by markedly prolonging acid contact time. It can be assumed that any hypnotic acting via similar CNS mechanisms would have a similar deleterious effect on sleep related GER. It should be noted that a "pharmaceutically effective amount" of baclofen, as the term is used herein and defined above, may or may not improve GER or GERD in these insomnia patients.

In another embodiment, a method for treating insomnia and nighttime GER or GERD is provided. The method comprises the step of administering a pharmaceutically effective amount of baclofen to an individual suffering from insomnia and nighttime GER or GERD. In this instance, the pharmaceutically effective amount of baclofen is also sufficient to treat the nighttime GER or GERD. For example, the pharmaceutically effective amount of baclofen is sufficient to improve one or more of the subjective or objective sleep parameter deficiencies associated with insomnia and this amount is also effective in reducing the acid contact time or number of reflux events associated with nighttime GER. In one aspect of this embodiment, the insomnia is primary insomnia and the nighttime GER or GERD exacerbates the insomnia.

Baclofen can be administered to the individual orally in pill form. Alternatively, baclofen can be administered by placing a transmucosal tablet, liquid, capsule or film sublingually or buccally. The dose of baclofen administered can be in the range from about 1 mg to about 60 mg. In some embodiments, the dose of baclofen can be in the ranges from about 5 mg to about 55 mg, from about 10 mg to about 50 mg, from about 15 mg to about 45 mg, from about 20 mg to about 40 mg, from about 25 mg to about 35 mg, and from 30 mg to about 32.5 mg including all doses between the above listed ranges. In yet another embodiment, the dose of baclofen is from about 10 mg to about 40 mg. Baclofen can be administered to the individual between 2 hours and 30 minutes prior to the desired sleep time. For example, baclofen can be administered one hour prior to the desired sleep time.

Baclofen may be formulated in a number of drug delivery systems. As a treatment for insomnia, it is important that the selected formulation possess a rapid and predictable onset of action while simultaneously possessing a half-life that permits sleep to be sustained for 7-8 hours. Thus, in one embodiment, baclofen is administered in an extended-release formulation. In one embodiment, baclofen can be provided in an oral delivery system. For example, the oral delivery system comprises a pill or capsule that is swallowed by the patient. In another aspect, the oral delivery system comprises a transmucosal tablet, liquid, capsule or film that can be placed sublingually or buccally. Alternatively, baclofen can be administered by an intramuscular, subcutaneous, or intravenous injection.

In one embodiment, baclofen is administered in a pharmaceutically effective amount to treat insomnia. In a preferred embodiment, baclofen is administered in a pharmaceutically effective amount to treat insomnia wherein the pharmaceutically effective amount does not cause undesirable side effects such as drowsiness and headache upon waking, parasomnias, amnesia, and prolongation of acid mucosal contact in the esophagus. The ranges of pharmaceutically effective amounts of baclofen can be from about the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 mg to about the groups consisting of 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 mg. In one embodiment, the range of pharmaceutically effective amounts of baclofen is from about 10 mg to about 40 mg.

It should be understood that a pharmaceutically effective amount of baclofen that does or does not cause undesirable side effects may comprise different doses based on an individual's characteristics including age, weight, drug tolerance, sex, ethnicity, and various genetic factors involved in the metabolism of baclofen. Accordingly, embodiments of the present method further comprise adjusting the dose of baclofen based on one or more factors of the group consisting of baclofen metabolite levels, age, weight, drug tolerance, sex, and presence of side effects upon waking.

Baclofen can be administered from about two hours to about thirty minutes from the desired onset of sleep. For example, baclofen can be administered one hour prior to desired onset of sleep. It should be understood that the precise timing of administration may be adjusted according to the individual's experiences with the drug. Moreover, the timing of administration will also be dependent on the drug delivery system. For example, sublingual or buccal administration of baclofen provides a more rapid delivery mechanism thereby potentially promoting onset of sleep in less than thirty minutes. Alternatively, simple ingestion of a capsule or tablet may promote sleep one to two hours thereafter.

EXAMPLE 1

The purpose of this example is to demonstrate the effectiveness of baclofen on sleep parameters in individuals subjected to a transient insomnia protocol.

Subjects

Twenty-four (24) healthy subjects aged 18-65 years (inclusive) with no insomnia were recruited for this study. Individuals were excluded if they regularly used medication with known CNS effects or had a history of sleep disorders including apnea, insomnia, narcolepsy, or restless legs syndrome. Individuals were also excluded if they had excessive daytime sleepiness indicated by an Epworth Sleepiness Score (ESS) of >9 or a chronic sleep disturbance indicated by a Pittsburgh Sleep Questionnaire Inventory (PSQI) score of >5. Shift workers or subjects with irregular sleep schedules were excluded. Women of child-bearing potential who used medically acceptable methods of contraception were allowed to participate. Subjects were excluded if they had any of the following: BMI≥30; symptoms of gastroesophageal reflux such as heartburn on a regular basis; history of allergic reaction or hyper-sensitivity to benzodiazepines or CNS depressants; or evidence of any clinically significant medical abnormality or chronic disease indicated on laboratory screen or physical exam. Subjects were also excluded if they had any of the following: a history of alcohol or drug abuse; consume >2 alcoholic beverages on a single day and >14 beverages weekly; or >5 cigarettes a day and could not forego smoking for up to 14 hours while in the sleep lab. Participants abstained from over-the-counter medications within 7 days of the polysomnographic (hereinafter "PSG") evaluation (except accepted birth control medication, NSAIDS/acetaminophen for infrequent pain not considered clinically significant). Participants abstained from alcohol for 24 hours and caffeine for 6 hours prior to each PSG evaluation. Eligible participants were required to report normal sleep patterns during the week before each PSG defined as a bedtime between 21:00 and 24:00 on at least 5 of 7 consecutive nights, with reported sleep duration between 7-9 hours, and no more than 2 naps a week. Participants were excluded if they failed the pre-PSG drug screen or had an apnea hypopnea index (AHI)>10 revealed on PSG.

Procedures

The present study was a single-site study approved by Aspire Institutional Review Board. The study design was a double blind cross-over study. Subjects gave written informed consent prior to any study-related procedures. The study consisted of a screening session and two overnight PSGs. The treatments consisted of baclofen 20 mg and placebo. The screening session consisted of a medical screening visit to determine eligibility and safety for each subject. Eligible subjects were randomized into two treatment sequences based on a random permutation algorithm. One treatment sequence received baclofen 20 mg on the night of the first PSG, then placebo on the night of the second PSG. The other treatment sequence received placebo on the night of the first PSG, then baclofen 20 mg on the night of the second PSG. Subjects were given a 7 day sleep diary to complete immediately prior to the first sleep study. Subjects were given a second 7 day sleep diary to complete immediately prior to the second sleep study. Lights out was determined as two hours earlier than the subject's median habitual bedtime indicated in the diary prior to each PSG. Study drug (baclofen 20 mg or placebo) was administered 90 minutes prior to lights out.

On the PSG nights, respiratory effort and airflow, oxygen saturation, leg and chin EMGs were recorded in addition to the routine PSG measures to exclude subjects with sleep-related breathing disorders and periodic limb movement disorder. Subjects were excluded if they had a mean AHI>10 or PLMAI>15. PSG measures consisted of the following: wake after sleep onset (WASO), total sleep time (TST), sleep onset latency (SOL), sleep efficiency (SE), percent sleep stage 1, percent sleep stage 2, percent sleep stages 3 and 4 combined, percent sleep REM. Self-report measures consisted of the following: subjective TST (sTST), subjective SOL (sSOL), subjective number of awakenings from sleep (sNAS), subjective sleep quality (sSQ). All PSGs were analyzed by one of the authors blinded to the treatment groups.

Dependent Measures

Hypnotic efficacy variables were extracted from standardized visual PSG scoring according to the scoring manual of the American Academy of Sleep Medicine (AASM) rules and included total sleep time (TST—time in minutes spent in NREM and REM sleep between Lights Out and Lights On), sleep onset latency (SOL—time in minutes from Lights Out to first epoch of sleep), sleep efficiency (SE—calculated by dividing TST by total recording time), and wake after sleep onset (WASO—number of minutes spent awake following sleep onset). Sleep architecture was assessed by calculating the percentage of TST spent in stage 1, stage 2, deep sleep (stage 3 and 4 combined), and REM. Self-reported (subjective) efficacy measures of sleep were collected on a morning questionnaire and included total sleep time (sTST), sleep onset latency (sSOL), number of awakenings from sleep (sNAS), and sleep quality (SQ based on a scale of 1-4; 1=good, 2=average, 3=below average, 4=poor).

Next day residual effects were assessed by a comparing pre- and post-PSG Digit Symbol Substitution Test (DSST; 90-s duration) and Symbol Copying Test (SCT; 90-s duration). Hangover effect of baclofen 20 mg was assessed by comparing a Visual Analog Scale (VAS) for sleepiness administered the morning after each PSG. DSST and SCT were administered prior to study medication provided 90 minutes before Lights Out. DSST, SCT, and VAS were conducted 30 minutes after Lights On in the order given. Subjects were contacted between 24-48 hours after each PSG to assess any side-effects or adverse events.

Statistical Analysis

The primary outcome variables were WASO, TST, and SE. Secondary outcome variables were SOL, sTST, sSOL, and sNAS. Exploratory variables to assess residual effects were cognitive and visual analog test scores (DSST, SCT, and VAS). Objective PSG measures such as the percent of time in each sleep stage, subjective self-reports, and residual effects were analyzed using SPSS 11.0 (SPSS Inc., Chicago, Ill., USA). Paired samples t-tests were used to compare means between treatment groups for normally distributed dependent measures. Wilcoxon signed-rank tests were used to compare the medians between treatment groups for non-normally distributed dependent measures. Sample size determination was made based on previous findings in our laboratory from a study of the effect of baclofen in patients with nighttime reflux.

Results

A total of 24 subjects were screened to randomize 22. Reasons for exclusion were failed pre-PSG drug screen (1) and failed BMI criteria. Of the 22 subjects randomized, two participants failed due to sleep apnea at the first PSG and were withdrawn from the study. The remaining 20 participants (8 males, 12 females) completed both PSGs and were included in data analysis. Patient characteristics are noted in Table 1.

TABLE 1

Demographic Data

| | |
|---|---|
| Sex | Males: 8 (40%); Females: 12 (60%) |
| Age | 33.4 ± 9.7 years; 20.8-53.6 years |
| Body Mass Index | 24.3 ± 3.0; 19.6-29.8 |

TABLE 1-continued

Demographic Data

| | |
|---|---|
| Epworth Sleepiness Score | 3.8 ± 2.5; 1-9 |
| Pittsburg Sleep Quality Index Score | 2.7 ± 1.4; 0-5 |

Values are presented as number (percentage of sample), or mean ± sd; range

Table 2 contains the descriptive data for the objective and subjective sleep parameters for placebo and 20 mg baclofen conditions. Objective PSG measures demonstrate significantly less WASO and Stage 1 sleep, and significantly longer TST, increased SE, and increased Stage 3/4 sleep in the baclofen 20 mg condition compared to placebo. Although not statistically significant, a decrease in stage 2 sleep and an increase in REM sleep were noted in the baclofen 20 mg condition compared to placebo (p=0.092, p=0.067, respectively). There was no significant effect of baclofen 20 mg on SOL. Subjective self-report variables collected on the morning questionnaire indicate significantly less sNAS and increased sSQ. There was no effect of baclofen on sTST or sSOL. There were no significant differences between treatment conditions in cognitive testing (DSST, SCT) or residual sleepiness testing (VAS). No serious adverse events were reported.

TABLE 2

Objective PSG and Subjective (self-report) measures

| | Placebo | Baclofen 20 mg | Absolute Change |
|---|---|---|---|
| PSG Measure | | | |
| WASO (min) | 54.0 ± 10.2 | 25.6 ± 4.0 | −28.4* |
| TST (min) | 407.7 ± 10.1 | 435.4 ± 5.8 | 27.7** |
| SOL (min) | 19.8 ± 2.9 | 19.4 ± 3.8 | −0.4 |
| SE (%) | 84.8 ± 2.1 | 90.6 ± 1.2 | 5.8** |
| Stage 1 (%) | 4.1 ± 0.4 | 2.3 ± 0.3 | −1.8*** |
| Stage 2 (%) | 62.8 ± 1.8 | 58.9 ± 2.0 | −3.9 |
| Stage 3/4 (%) | 12.0 ± 1.3 | 14.7 ± 1.4 | 2.7* |
| REM (%) | 20.6 ± 1.6 | 24.1 ± 1.3 | 3.5 |
| Self-Report Variable | | | |
| sTST (h) | 6.8 ± 0.2 | 7.1 ± 0.2 | 0.3 |
| sSOL (min) | 26.0 ± 2.9 | 25.0 ± 4.1 | −1.0 |
| sNAS (#) | 3.7 ± 0.2 | 2.4 ± 0.4 | −1.3** |
| sSQ (scale 1-4) | 2.4 ± 0.2 | 1.9 ± 0.2 | −0.5* |

1 = good,
2 = average,
3 = below average,
4 = poor
*p < 0.05;
**p < 0.01;
***p < 0.001

Discussion

This study showed baclofen to be significantly superior to placebo with regard to several commonly used measures to assess sleep quality. More specifically, regarding objective PSG measures, baclofen revealed significant improvement in TST, WASO, and SE. In addition, several other PSG parameters were notably improved such as a significant decrease in stage 1 sleep and an increase in stages 3+4 sleep. Importantly, the subjective measures also showed significant improvement so that both objective and subjective measures of sleep quality were aligned. These results lend strong support for baclofen as an effective hypnotic drug.

These results demonstrate that baclofen unexpectedly performs better than other hypnotic drugs using the same transient insomnia model as shown in Table 3. The up arrows indicate an increase in the parameter for subjects who were in the drug condition, compared to placebo condition and the down arrows indicate a decrease in the parameter for subjects who were in the drug condition, compared to placebo condition. For example in the two studies which used the exact same phase advance (2 hrs.), the data provided in the present study for baclofen is far superior to both doses of indiplon in terms of both an increase in TST and decrease in WASO. The indiplon study did not report data on SE. Compared to the study on zolpidem, the present baclofen data again is clearly superior in terms of both WASO and SE. Data on TST were not reported. In addition, baclofen performed substantially better than zolpidem, which is the largest selling hypnotic drug in the US. Specifically, the decrease in WASO was only 9.4 min. and the increase in SE was only 3.7% with zolpidem. The present baclofen data are 2-4-fold better. Even with a 3 hr. phase advance model (which should allow even more positive results than a 2 hr. phase advance) the baclofen data in this study are consistently more positive compared to several doses of zolpidem. For example, only the highest dose of zolpidem (20 mg) showed a significant reduction in WASO but this dose did not show a significant improvement in TST. The design of this zolpidem study should be noted in that it is, similar to the present study, a single site cross-over design. The present data on the subjective reports on sleep quality is also impressive for a short study with a relatively small number of participants. Although the subjective TST and SOL were not significant, the arousals from sleep (sNAS) and the overall quality of sleep were significantly improved.

TABLE 3

Comparison of the effect of baclofen on sleep versus other common hypnotics

| Drug | Study Population | TST | WASG | SOL | SE | Reference | Sample | Design |
|---|---|---|---|---|---|---|---|---|
| Baclofen 20 mg | 2 hour phase-advance | ↑ 27.7 | ↓ 28.3 | ↓ 0.4$^{NS}$ | ↑ 5.8 | Orr et al., current study | N = 20, 1 site | Cross-over |
| Doxepin 6 mg | 3 hour phase-advance | ↑ 51.1 | ↓ 40.0 | ↓ 15.9 | ↑ 10.7 | Roth et al., 2010 | M = 565, 6 sites | Parallel group |
| Ramelteon 8 mg | First-night effect (no PA) | ↑ 17.1 | ↓ 5.0$^{NS}$ | N/A | ↑ 3.2 | Zammit et al., 2009 | N = 289, multi-site | Parallel group |
| Ramelteon 16 mg | | ↑ 13.4 | ↓ 2.5$^{NS}$ | N/A | ↑ 2.4$^{NS}$ | | | |
| Indiplon 10 mg | 2 hour phase-advance | ↑ 11.6 | ↓ 1.2$^{NS}$ | N/A | N/A | Rosenberg et al., 2007 | N = 593, 18 sites | Parallel group |
| Indiplon 20 mg | | ↑ 20.6 | ↓ 7.4 | N/A | N/A | | | |

TABLE 3-continued

Comparison of the effect of baclofen on sleep versus other common hypnotics

| Drug | Study Population | TST | WASG | SOL | SE | Reference | Sample | Design |
|---|---|---|---|---|---|---|---|---|
| Zolpidem 10 mg | 2 hour phase-advance | N/A | ↓ 9.4 | N/A | ↑ 3.7 | Erman et al., 2001 | N = 630, 13 sites | Parallel group |
| Zolpidem 5 mg | 3 hour phase-advance | ↑ 35.6$^{NS}$ | ↓ 22.5$^{NS}$ | N/A | N/A | Walsh et al., 1990 | N = 30, 1 site | Cross-over |
| Zolpidem 10 mg | | ↑ 35.7 | ↓ 31.2$^{NS}$ | N/A | N/A | | | |
| Zolpidem 15 mg | | ↑ 37.3 | ↓ 26.9$^{NS}$ | N/A | N/A | | | |
| Zolpidem 20 mg | | ↑ 12.8$^{NS}$ | ↓ 32.3 | N/A | N/A | | | |
| Zolpidem 10 mg | 4 hour phase-advance | ↑ 52.8 | ↓ 35.1 | N/A | N/A | Walsh et al., 2007 | N = 109, 6 sites | Cross-over |
| Zolpidem 10 mg | 4 hour phase-advance | ↑ 47.8 | ↓ 24.7 | N/A | N/A | Svetnik et al., 2010 | M = 55, 6 sites | Cross-over |
| Temazepam 15 mg | 2 hour phase-advance | N/A | ↓ 7.0$^{NS}$ | N/A | ↑ 2.5 | Erman et al, 2001 | ft = 530, 13 sites | Parallel group |

$^{NS}$NOT SIGNIFICANTLY DIFFERENT COMPARED TO PLACEBO

Regarding the SOL measure, neither objective nor subjective SOL was significantly improved with baclofen. This could be explained by the fact that the SOL was within normal limits under placebo conditions with both objective and subjective measures. In the present study, the objective SOL was approximately 19 minutes. Thus, the 2 hr. phase advance model was not sufficient to produce a substantial delay in sleep onset. Under these circumstances, a significant drug effect would not be expected.

In conclusion, baclofen produced very significant improvements in both objective and subjective sleep measures compared to placebo. In addition, compared to other data on currently available hypnotic drugs, baclofen appears to be superior when comparisons are made using a similar phase advance study model.

EXAMPLE 2

The purpose of this example is to demonstrate the effect of baclofen on acid contact time and the number of reflux events during sleep.

Participants

Individuals aged 18-65 (inclusive) with complaints of nighttime heartburn or regurgitation at least twice per week and a Carlsson GERD score of at least 5 were invited to participate. Individuals were excluded if they had a history of significant gastric or esophageal disease, sleep disorders such as obstructive sleep apnea or narcolepsy, or any significant medical disorder. Participants were also excluded if they took sedating medications on a regular basis (PRN use was allowed if they agreed to abstain from use on the nights in the sleep laboratory). Participants were recruited from a database of patients with heartburn complaints. These participants had previously expressed interest in participating in medical research studies at our facility. Advertising was not utilized in recruitment.

Procedures

Esophageal pH monitoring was performed using an antimony pH catheter (Sandhill Scientific, Highlands Ranch, Colo., USA) placed in the distal esophagus. The catheter was inserted into the esophagus via the nares and positioned so that the pH electrode was 5 cm above the manometrically determined LES. Prior to insertion the pH electrode was calibrated against solutions of pH 4 and 7. The catheter was connected to an acid reflux monitor, which allowed continuous recordings of esophageal pH for a 24-hour period as well as simultaneous pH monitoring during PSG (ZepHr, Sandhill Scientific).

Data were analyzed using BioVIEW Analysis software (Sandhill Scientific). This software provides a report of upright, supine, and total acid contact time (ACT), which were used as outcome measures in the study.

Overnight polysomnography included monitoring of electroencephalography, electroocculography, submental electromyography, airflow (thermistor), electrocardiogram and SaO2. Distal and proximal pH was also recorded via the polysomnography system. These data were collected on a computerized data acquisition system (Grass Telefactor, Aurora polysomnographic systems, West Warwick, R.I., USA). "Lights Out" occurred at the patient's usual bedtime. Time in bed was standardized to 8 hours. For the purposes of this study, significant sleep apnea was defined as an apnea hypopnea index (AHI) of at least 10 events per hour of sleep. Individuals with an AHI of 10 or greater on the first sleep study were excluded from the study. Likewise, individuals with a periodic limb movement arousal index (PLMAI) of 10 or greater were excluded.

A reflux event was defined as a period of at least 30 consecutive seconds with pH readings below 4. A reflux event ended when the pH rose to 4 or greater for a period of at least 30 seconds. Reflux events were only counted if they occurred after PSG documented sleep onset had occurred. These analyses were done by hand in order to determine which events occurred during sleep and which occurred during wake.

The Carlsson GERD questionnaire is a 7-item measure of symptoms consistent with GERD. This was used as a screening tool to identify participants who were likely to be diagnosed with GERD (a score of 5 or greater was required to participate in the study).

This study was a cross-over trial in which all participants received both treatments (baclofen and placebo), in random order. Study medication was given on the two nights of the combined pH/PSG, with baclofen (40 mg) on one occasion and placebo on the other, in random order (see FIG. 1).

Written, informed consent was obtained from all participants before any study-related procedures were performed. At the initial visit subjects underwent a physical examination, blood work (complete blood count, complete metabolic panel), and urine drug screens. In addition, participants completed the GER questionnaires. Individuals who were taking GER medications were required to cease taking these medications (10-14 days washout period for PPIs, 48 hours for H2 receptor antagonists, and 24 hours for over-the-counter antacids).

The second and third visits were scheduled one to two weeks after the initial visit, and were separated by a washout period of approximately one week. Total time in the study was thus approximately two to three weeks. At these visits, participants were intubated with the pH sensor at approximately eight a.m. Participants returned approximately two hours before their normal bedtime for the PSG. Patients were provided with either baclofen (40 mg) or placebo in a randomized, cross-over fashion 90 minutes before bed by the PSG technician. Both participants and PSG technicians were blinded to the condition (baclofen or placebo). Baclofen and placebo were white pills that were identical in appearance. The order of medication was determined by a computer-generated list of random sequences.

All participants were given a reflux-provoking meal consisting of one regular quarter pound hamburger with cheese, a blueberry muffin, and an 8 oz cola (non-caffeinated). The meal occurred 60 minutes before bedtime. In the morning after the PSG, the sleep quality questionnaire was administered.

Statistical Analyses

For the number of reflux events, assuming a standard deviation of 4 and a minimum detectable difference of 4 reflux events, 14 participants would be needed to have 80% power to detect a difference at the 0.05 significance level (one-tailed test).

The primary outcome variable was the number of recumbent reflux events. A p-value of <0.05 was considered significant for all statistical tests. Statistical analyses were conducted using SPSS 11.0 (SPSS Inc., Chicago, Ill., USA).

Although there was a one-week washout between treatment conditions which should have prevented any carryover effects, statistical analyses were conducted to ensure that no order or carryover effects occurred. Specifically, to detect order effects, the change score between placebo and drug conditions was calculated, and an independent t test on the change score for each outcome variable was conducted (e.g., number of reflux events, total sleep time, etc.) with order as the independent variable. To detect carryover effects, a new variable was created with scores for each outcome for each period in the study (periods one and two). A dependent t test was done on each outcome variable according to period.

No changes to the methods or trial outcomes were made after the study was begun. The trial ended when 21 patients had completed the study as needed according to the power analysis.

Results

Thirty-four individuals entered the study. Of these 34, eight individuals did not meet study criteria (six failed a urine drug screen, and two failed for presence of a sleep disorder). Therefore, 26 individuals were randomized into the study. An additional three participants screen failed due to sleep apnea at the first PSG, one patient dropped due to schedule conflicts after PSG 1, and one patient dropped due to intolerance of the pH probe. Twenty-one participants completed the study and were included in the analysis (12 received placebo first, and nine received drug first). Prior to entry into the study, 3 (14%) were taking no medication for their GER, 7 (33%) were taking PPIs, 4 (19%) were taking H2 blockers, and 6 (29%) were taking over-the-counter medications. No adverse events were documented.

There were no significant order effects or carryover effects for any outcome variable (all p>0.05). As shown in FIG. 1A, baclofen reduced the number of distal reflux events occurring after PSG-determined sleep onset by 56% compared to placebo (p<0.05). Reflux events occurred during sleep as well as during wakefulness, but were significantly fewer in number during sleep (p<0.05) as depicted in FIG. 1B. Compared to placebo, baclofen reduced reflux events which were associated with wakefulness as well as those associated with sleep. See FIG. 1C.

The number of reflux events occurring during sleep preceded by a brief awakening or arousal was also assessed. If an awakening or arousal was found within two minutes of the beginning of a reflux event, it was counted. With these criteria, the majority of reflux events occurring during sleep (55%) were associated with a brief awakening or arousal. This is consistent with other studies which have documented evidence that most reflux occurs during wakefulness or brief awakenings from sleep. Although not statistically significant, recumbent ACT was decreased by approximately 50% with baclofen versus placebo as shown in FIG. 1D.

Discussion

This study demonstrated that baclofen (40 mg) significantly reduced the number of sleep-related reflux events, and showed a strong tendency to reduce ACT, as compared to placebo. The lack of statistical significance on ACT is most likely due to the very large and characteristic variance in these measures. These results are similar to those of previous studies which have shown that baclofen administration significantly inhibits reflux events. Using the same acute dose as used in the present study (40 mg), Lidums et. al., Gastroenterol 2000; 118: 7-13, also noted a significant reduction in postprandial reflux events and no significant change in ACT in normal participants. The present results have shown an absolute reduction in reflux events of 56% with baclofen vs. placebo which is actually superior to that noted in other studies which have shown decreases in the range of 40%.

The results in Example 2 demonstrate that baclofen significantly decreases the number of reflux events experienced during sleep. Considering this in view of the significant effects baclofen demonstrated in directly improving sleep parameters in Example 1, baclofen demonstrates therapeutic potential as a treatment for insomnia in patients that also suffer from nighttime GER.

While the foregoing description enables one of ordinary skill in the art to make and use the methods described herein, those of ordinary skill will understand and appreciate the existence of variations, combinations, and equivalents of the embodiments described herein. The invention should therefore not be limited by the above description, but by the scope and spirit of the invention as claimed.

What is claimed is:

1. A method for treating insomnia comprising the step of administering a pharmaceutically effective amount of baclofen to an individual suffering from insomnia in order to treat the insomnia, wherein the baclofen is selected from the group consisting of 4-amino-3-(4-chlorophenyl)-butanoic acid including R-baclofen and S-baclofen, pharmaceutically acceptable salts thereof, prodrugs thereof, and mixtures thereof.

2. The method of claim 1, wherein the insomnia is primary insomnia.

3. The method of claim 1 wherein the insomnia is chronic insomnia.

4. The method of claim 1 wherein the individual also suffers from sleep-related gastroesophageal reflux.

5. The method of claim 1, wherein the individual also suffers from sleep-related gastroesophageal reflux and wherein the pharmaceutically effective amount of baclofen is also sufficient to treat sleep related gastroesophageal reflux.

6. The method of claim 1, wherein the individual also suffers from gastroesophageal reflux disease and wherein the pharmaceutically effective amount of baclofen is also sufficient to treat related gastroesophageal reflux disease.

7. The method of claim 6, wherein the step of administering is performed from about 2 hours to about 30 minutes prior to desired onset of sleep.

8. The method of claim 6, wherein the pharmaceutically effective amount of baclofen is in a range of from about 1 mg to about 60 mg.

9. The method of claim 8, wherein the pharmaceutically effective amount of baclofen is in a range of from about 15 mg to about 45 mg.

10. The method of claim 8, wherein the pharmaceutically effective amount of baclofen is in a range of from about 30 mg to about 35 mg.

* * * * *